United States Patent [19]
Moon

[11] Patent Number: 5,992,505
[45] Date of Patent: Nov. 30, 1999

[54] FOULING MONITORING APPARATUS OF HEAT EXCHANGER AND METHOD THEREOF

[75] Inventor: Jeon-Soo Moon, Taejeon, Rep. of Korea

[73] Assignee: Korea Electric Power Corp., Seoul, Rep. of Korea

[21] Appl. No.: 08/909,843

[22] Filed: Aug. 12, 1997

[30] Foreign Application Priority Data

Aug. 13, 1996 [KR] Rep. of Korea ..................... 96-33524

[51] Int. Cl.⁶ .................................................. F28F 17/00
[52] U.S. Cl. ............................................ 165/11.1; 165/95
[58] Field of Search .................................. 165/11.1, 11.2, 165/95

[56] References Cited

U.S. PATENT DOCUMENTS

| | | | |
|---|---|---|---|
| 4,485,449 | 11/1984 | Knauss | 364/510 |
| 4,755,533 | 7/1988 | Kaya | 364/506 |
| 5,615,733 | 4/1997 | Yang | 165/11.1 |
| 5,677,677 | 10/1997 | Duff | 340/585 |
| 5,713,668 | 2/1998 | Lunghofer et al. | 374/179 |

OTHER PUBLICATIONS

Andrew D. Althouse, et al., Modern Refrigeration and Air Conditioning, The Goodheart–Willcox Company, Inc., 1988.

Primary Examiner—Ira S. Lazarus
Assistant Examiner—Lance Chandler
Attorney, Agent, or Firm—Watson Cole Grindle Watson, PLLC

[57] ABSTRACT

An apparatus for measuring a fouling resistance and a cleanliness factor of heat-transfer surface and which is capable of continuously and accurately monitoring a build-up degree of deposits on a heat-transfer surface of a heat exchanger includes a fouling sensor having a given length of metal wire wound inside the heat-transfer surface for measuring an average temperature of the heat-transfer surface, a direct current voltage supply member for supplying a voltage to a heating wire of the fouling sensor, an accurate resistance measuring member connected with a temperature measuring metal wire of the fouling sensor for measuring an electrical resistance of the metal wire, an inlet/outlet portion water temperature measuring member for measuring the temperatures of the inlet/outlet portions of the apparatus, a water flow rate measuring member, and a data calculation apparatus for computing a fouling resistance and a cleanliness factor of a heat-transfer surface.

10 Claims, 3 Drawing Sheets

FOULING MONITORING APPARATUS OF HEAT EXCHANGER AND METHOD THEREOF

BACKGROUND OF THE INVENTION

1. Application Fields of the Invention

The present invention relates to an apparatus and method for monitoring fouling resistance and cleanliness factor of a heat-transfer surface of a heat exchanger, and in particular, to an improved system for monitoring the precise fouling tendency on a heat-transfer surface of a heat exchanger and a method thereof which are capable of continuously and accurately observing scale deposition in a heat exchanger due to hardness components and suspended solids contained in cooling water by measuring an average temperature on the heat-transfer surface of a heat exchanger.

2. Description of the Conventional Art

A plurality of heat exchangers are used in cooling systems of power plants, and petro-chemical plants. Since there are various impurities in cooling water such as dusts, suspended solids, microorganisms, and metal oxides, when cooling water containing impurities flows in the heat exchanger, scales and deposits are usually formed on a high temperature heat-transfer surface or in a low flow rate zone of the heat exchanger. The thusly-formed scales cause a decrease in heat-transfer efficiency of the heat exchanger and increase the flow resistance of a liquid.

Scale components which cause deposit formation on a heat-transfer surface of a heat exchanger include minerals such as calcite, whitlockits, gypsum, sepiolite, iron oxides, silica, etc. These scales are produced by the following chemical reactions.

i) Calcite

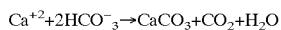

$$Ca^{+2}+2HCO^-_3 \rightarrow CaCO_3+CO_2+H_2O$$

ii) Hydroxyapatite/whitlockits

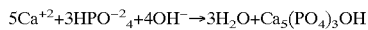

$$5Ca^{+2}+3HPO^{-2}_4+4OH^- \rightarrow 3H_2O+Ca_5(PO_4)_3OH$$

iii) Gypsum

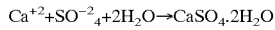

$$Ca^{+2}+SO^{-2}_4+2H_2O \rightarrow CaSO_4.2H_2O$$

iv) Sepiolite

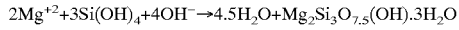

$$2Mg^{+2}+3Si(OH)_4+4OH^- \rightarrow 4.5H_2O+Mg_2Si_3O_{7.5}(OH).3H_2O$$

As shown in Table 1, since the above-described scale components have relatively low heat-transfer coefficients compared to metals, when such scale components deposit on the heat-transfer surface of the heat exchanger, the heat-transfer efficiency of the heat exchanger decreases.

TABLE 1 heat-transfer coefficients of typical metals and scales

| Classification | | Thermal transfer coefficient |
|---|---|---|
| Metal | Al-Brass | 700 |
| | Cu—Ni (70:30) | 310 |
| Scale | Calcite | 3 |
| | Whitlockits | 26 |
| | Gypsum | 18 |
| | Oxidized steel | 7 |

Therefore, in order to prevent the efficiency of the heat exchanger from decreasing due to scale deposits on the heat-transfer surface of the heat exchanger, a fouling monitoring system is used. The water treatment method of a cooling system can be improved based on the thusly-measured results which are obtained by the fouling monitor, and a proper cleaning period of the heat exchanger tube and an efficiency of the heat exchanger are determined.

In addition, Table 2 illustrates the operation values of fouling resistances of the heat exchanger which is generally applied in the industry. As shown therein, the fouling resistance coefficients are different in accordance with the kinds of liquids which pass through the heat exchanger. Actually, during the operation of the heat exchanger, the heat exchanger should be operated within the permitted fouling resistance values thereof so that the heat exchanger is not fouled excessively, whereby it is possible to obtain the design efficiency of heat exchangers.

TABLE 2

Typical operation limits of heat exchanger fouling resistance

| Tube-side liquid\ Cell-side liquid | Vapor | Liquid | Two-phase state of Vapor and liquid |
|---|---|---|---|
| Vapor | 3.9 | 5.1 | 6.0 |
| Liquid | 5.1 | 6.7 | 7.9 |
| Two-phase state of vapor and liquid | 4.8 | 5.1 | 6.5 |

With a conventional method for monitoring the fouling resistance of the heat exchanger due to the impurities contained in water, the deposit formation conditions on the heat-transfer surface of a heat exchanger can be visually observed or a surface analysis of the heat exchanger tube can be performed or the deposit weight thereon can be measured. However, with these methods, it is impossible to continuously monitor deposit formation while the system is being operated. In order to monitor the fouling resistance, the operation of the system should be shut down.

In addition, in order to overcome the above-described problems, an apparatus is disclosed for monitoring a deposit build-up by inserting a thermocouple in the heat-transfer surface of the heat exchanger. FIG. 1 illustrates a conventional apparatus for checking deposit formation on the heat-transfer surface of the heat exchanger. As shown therein, in an inlet of the apparatus an inlet temperature sensor 1 and an outlet temperature sensor 2 are installed for measuring the temperature of the inlet and output portions of the apparatus. A temperature sensor (thermocouple, Pt-100Ω, thermister) 6 is inserted in the heat-transfer surface 5 of the heat exchanger disposed within an outer circumferential surface of the heating element 4, which generates heat by power supplied from a power supply unit 1, and then the temperature variation of the heat-transfer surface is measured, thus checking the fouling resistance of the heat exchanger.

As shown in FIG. 1, in the conventional apparatus for monitoring a deposit formation an inlet temperature sensor and an outlet temperature sensor 2 are disposed in inlet and outlet portions of the apparatus for measuring water temperature. A temperature sensor [(thermocouple), Pt-100Ω, thermister] 6 is inserted in a heat-transfer surface 5 of a heat exchanger on an outer circumferential surface of a heating element 4 which generates heat by electric power supplied from a power supply unit 3, so that a temperature variation of the heat-transfer surface of the heat exchanger is measured and the fouling resistance of the heat exchanger is monitored.

As shown in FIG. 1, the heat generated by the heating element 4 is heat-exchanged with the cooling water flowing through the heat-transfer surface 5 of the heat exchanger. If scales having low heat-transfer coefficients are formed on the heat-transfer surface 5, the heat transfer rate of the heat-transfer surface 5 is inhibited, and the heat is not transferred to the cooling water, thus increasing the temperature of the heat-transfer surface 5. As the thickness of the scale is increased, the heat transfered to the cooling water is decreased, and the amount of heat insulated by the scale is gradually increased, whereby the temperature of the heat-transfer surface 5 is increased. At this time, the temperature variation of the heat-transfer surface 5 is directly influenced by the thickness of the scales which inhibits a heat-transfer, namely, by the fouling resistance of the heat-transfer surface 5. The temperature sensor 6 is installed on the heat-transfer surface 5 based on the condition that the temperature of the heat-transfer surface 5 is varied by the fouling resistance of the heat-transfer surface 5, thus measuring the temperature variation of the heat-transfer surface 5, so that the fouling resistance of the heat-transfer surface of the heat exchanger is measured.

However, the conventional fouling resistance monitoring method has the following problems.

First, the conventional fouling monitoring method which uses the temperature sensor 6 installed within the heat-transfer surface 5 is capable of detecting an increase of fouling resistance only when great amounts of scale are formed on the heat-transfer surface. When a small amount of scale is formed on the heat-transfer surface 5, it is impossible to check the temperature variation of the heat-transfer surface 5, and it is impossible to accurately monitor the fouling resistance thereon.

Second, since the scales are not uniformly formed on the heat-transfer surface, an erroneous measured fouling resistance, based on the position of the temperature sensor 6, may be measured.

Factors which cause a fouling resistance of the heat exchanger include the condition of the heat-transfer surface, the flow rate of water, and the water quality. Since the above-described factors are not uniformly applied to the whole heat-transfer surface, the scales are not uniformly formed on the heat-transfer surface. Namely, the scales formed on the heat-transfer surface may be detached therefrom when water flows at high speed, and the thickness of the scales may be increased when water flows at low speed. Under an experiment conducted therefor, the scales were not uniformly formed on the heat-transfer surface. If the fouling resistance is computed based on the erroneously measured temperature at only one point, the fouling resistance may become a factor which causes a serious problem.

FIGS. 2A through 2C illustrate operational principles with respect to a conventional fouling monitoring apparatus. FIG. 2A illustrates a case where the heat-transfer surface 5 is not fouled, and FIG. 2B illustrates a case where scales are uniformly formed on the heat-transfer surface 5. In this case, the temperature measured by the temperature sensor 6 may be considered as a representative temperature of the heat-transfer surface 5. However, as shown in FIG. 2C, if the scales are partially formed on the heat-transfer surface, the temperatures measured in accordance with the installation position of the temperature sensor 6 are different from each other. Therefore, there may be serious errors in the fouling resistance calculated by the measured values.

SUMMARY OF THE INVENTION

Accordingly, it is an object of the present invention to provide an apparatus for monitoring a fouling resistance and a cleanliness factor on a heat-transfer surface of a heat exchanger and a method thereof which overcome the aforementioned problems encountered in the conventional art.

It is another object of the present invention to provide an improved apparatus for monitoring deposit formation on a heat-transfer surface of a heat exchanger which is capable of continuously and accurately monitoring deposit formation in a heat exchanger due to foreign matter contained in the water in a cooling system by using an average temperature measuring method with respect to the whole heat-transfer surface.

To achieve the above objects, there is provided an apparatus for monitoring a deposit formation on a heat-transfer surface of a heat exchanger which includes a fouling sensor having a metal wire which is spirally and uniformly wound on outer circumferential surfaces of a heating wire, for measuring an average temperature of a heat-transfer surface of a heat exchanger, the direct current power supply member for supplying a voltage to a heating wire of the fouling sensor, an accurate resistance measuring member connected with the temperature measuring metal wire of the fouling sensor for measuring an electrical resistance of the metal wire, an inlet/outlet portion water temperature measuring member for measuring the temperatures of the inlet/outlet portions of the apparatus, a flow rate measuring member for measuring the flow rate introduced into the apparatus and controlling the amount of flowing water, and a data calculation apparatus for computing a fouling resistance and a cleanliness factor on a heat-transfer surface of the heat exchanger by using analog output signals outputted from the fouling sensor, the direct current static voltage supply member, the accurate resistance measuring member, the inlet/outlet portion water temperature measuring member and the water flow rate measuring member.

To achieve the above objects, there is provided a method for monitoring a deposit formation on a heat-transfer surface of a heat exchanger which includes the steps of disposing a metal wire having a high resistance temperature coefficient around a heat-transfer surface of a heat exchanger at a predetermined interval, measuring an electrical resistance variation of the metal wire, computing an average temperature of a whole heat-transfer surface based on the electrical resistance value of the metal wire, and computing a fouling resistance coefficient and a cleanliness factor with respect to the heat-transfer surface of the heat exchanger.

Additional advantages, objects and other features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The apparatus for monitoring a deposit formation and a method thereof according to the present invention will now be explained with reference to the accompanying drawings.

Figure 1:
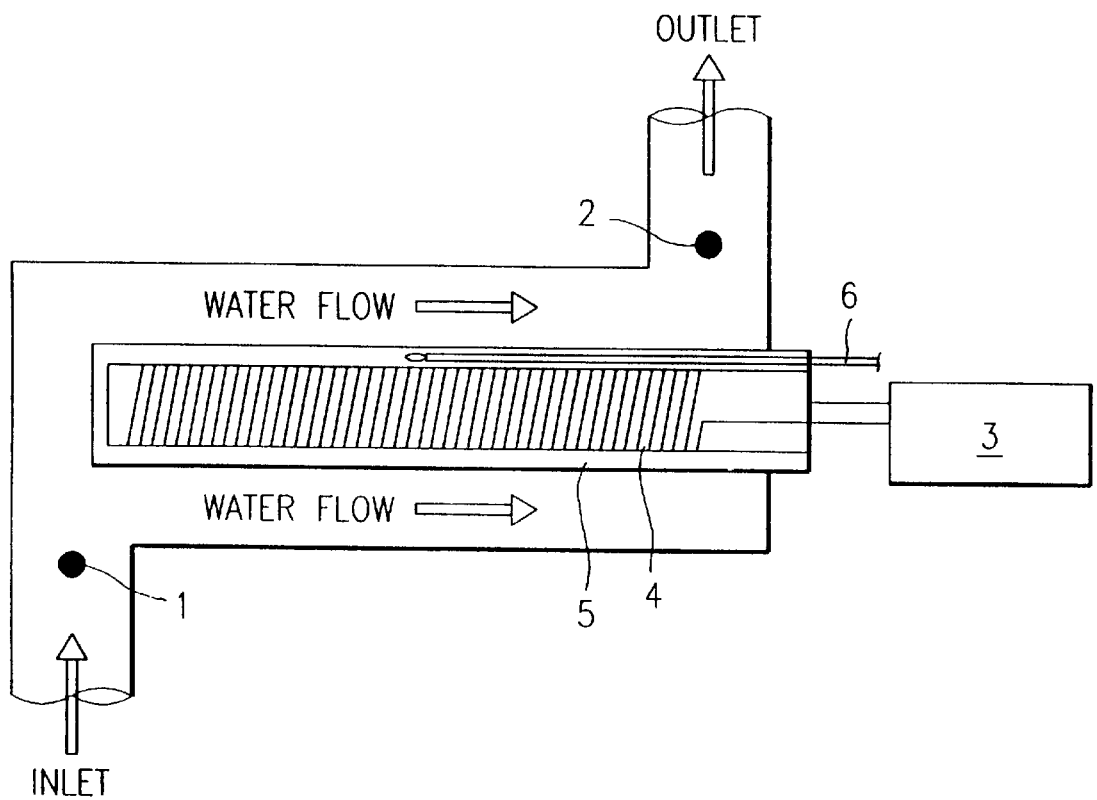
FIG. 1 is a view illustrating a conventional apparatus for monitoring a fouling resistance and a cleanliness factor.
Figure 2A:
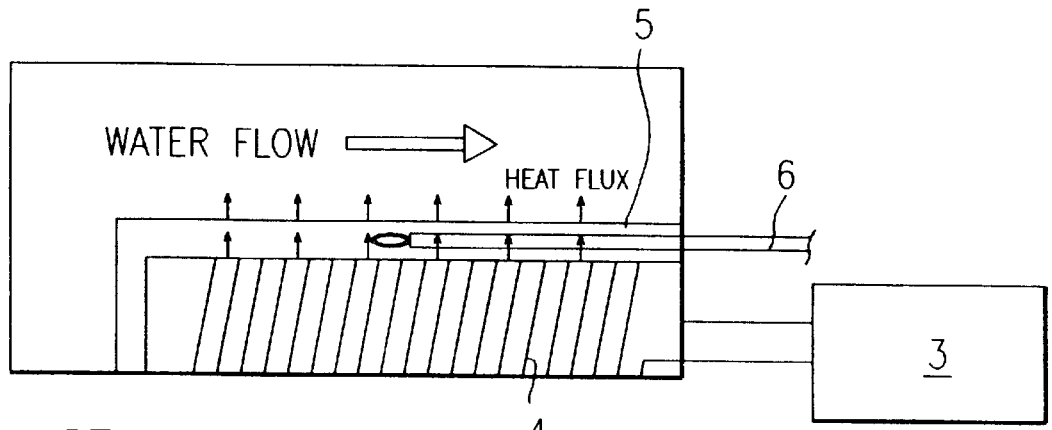
FIGS. 2A and 2C are views illustrating an operation principle of a conventional apparatus for monitoring a deposit formation.
Figure 2B:
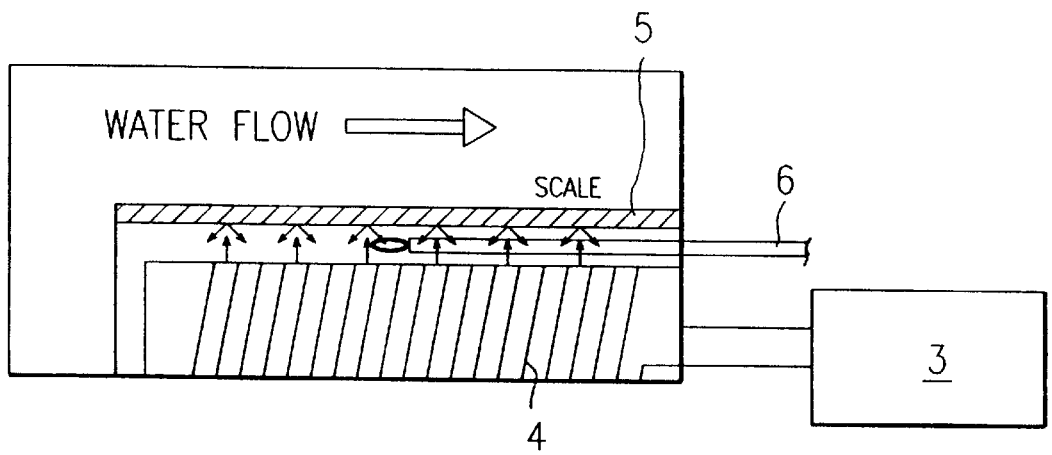
Figure 2C:
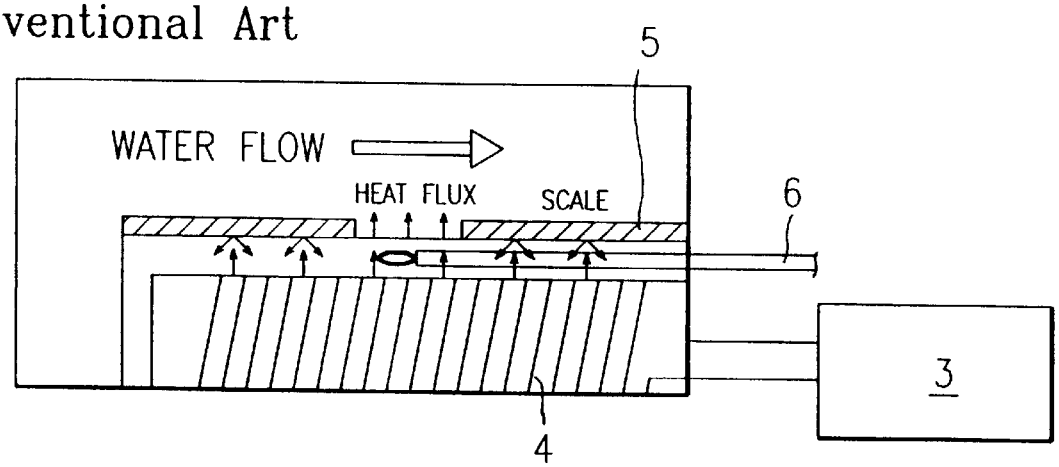
Figure 3:
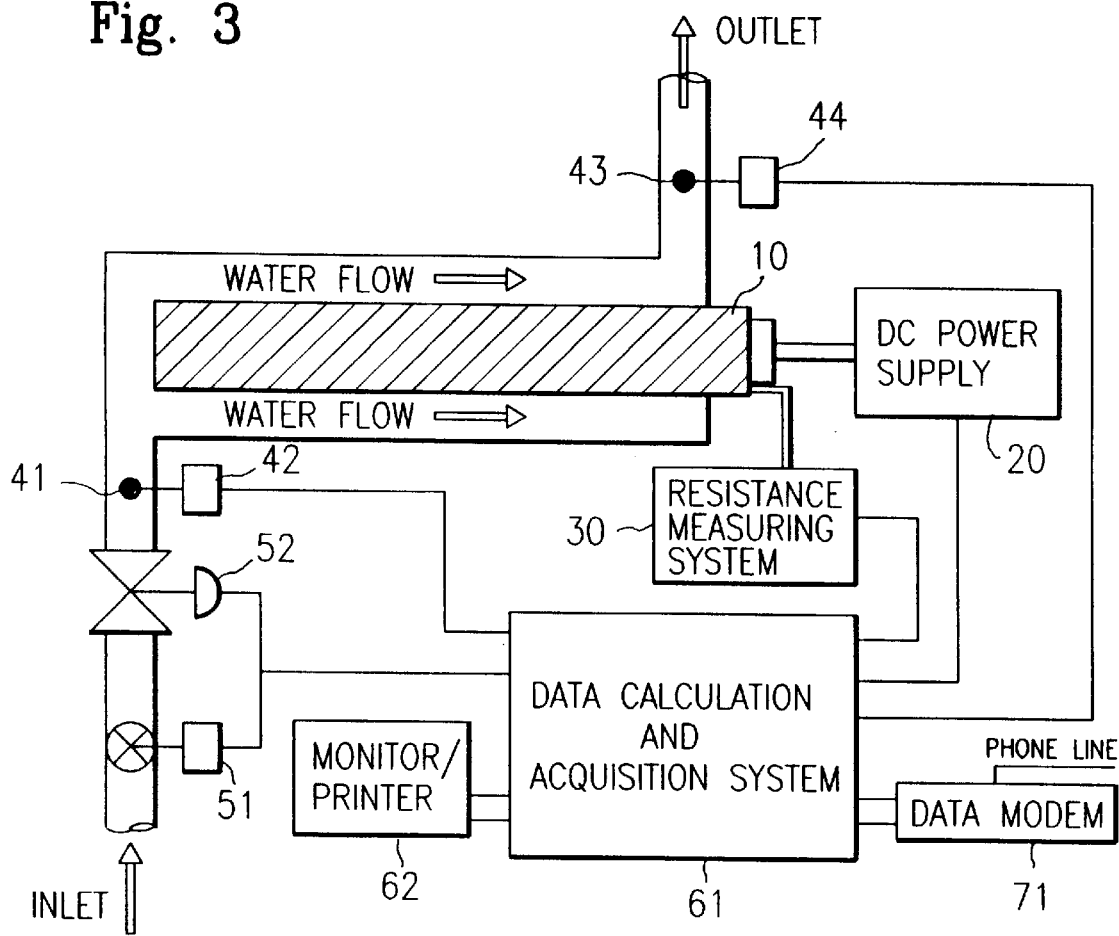
FIG. 3 is a schematic view illustrating an apparatus for monitoring a fouling resistance and a cleanliness factor on a heat-transfer surface of a heat exchanger according to the present invention.

FIG. 3 illustrates an apparatus for monitoring a fouling resistance and a cleanliness factor on a heat-transfer surface of a heat exchanger according to the present invention.

As shown therein, the apparatus for monitoring a deposit formation on a heat-transfer surface of a heat exchanger according to the present invention includes a fouling sensor 10 having a metal wire which is spirally wound on outer surfaces of a heating wire for measuring a temperature of a heat-transfer surface as a variation of a resistance value of a metal wire, a current power supply member 20 for supplying a voltage to the heating wire of the fouling sensor 10, an accurate resistance measuring member 30 connected with a metal wire which is formed to measure a temperature of the fouling sensor 10 for measuring an electrical resistance of the metal wire, an inlet/outlet portion water temperature measuring member having an inlet temperature sensor 41, a first signal transmitter 42, an outlet temperature sensor 43, and a second signal transmitter 44 for measuring a temperature at the inlet and outlet portions of the apparatus, a water flow rate measuring member having a flow sensor 51 and a flow control valve 52 for controlling the flowing amount by detecting the amount of flowing water introduced into the apparatus, and a data calculation apparatus which has a data calculation unit 61 having a memory device, and a monitor and printer 62 for displaying a currently measured data and a computation result and printing the results thereof, for computing a fouling resistance and a cleanliness factor with respect to a heat-transfer surface of the heat exchanger by using analog output signals from the fouling sensor 10, a direct current power supply member 20, an accurate resistance measuring member 30, and an inlet/outlet water temperature measuring member and a water flow rate measuring and controlling member.

At this time, the data calculation apparatus may be provided with a modem 71 for monitoring the data obtained by the fouling monitoring apparatus and computation results by a remote personal computer.

Figure 4:
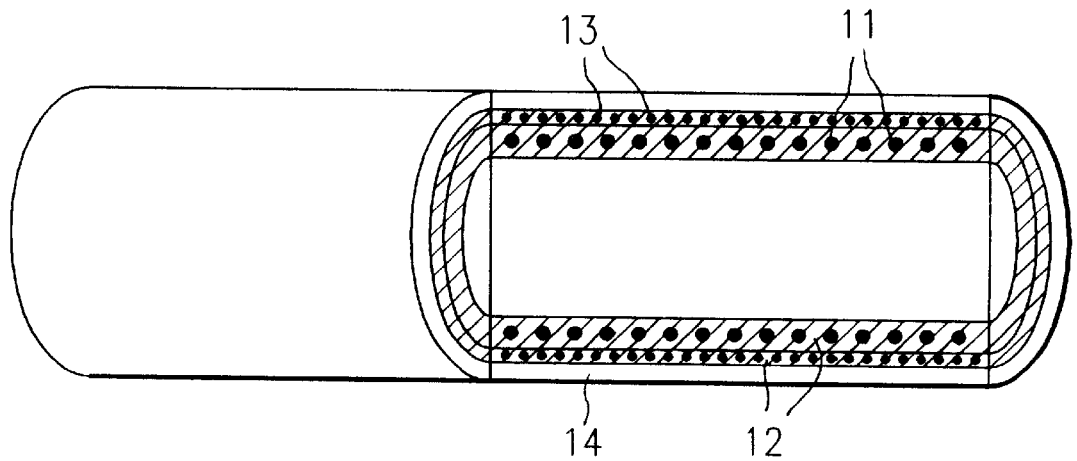
FIG. 4 is a partial cross-sectional view illustrating a fouling sensor which is an element of an apparatus for monitoring a deposit formation on a heat-transfer surface of a heat exchanger according to the present invention.

FIG. 4 illustrates a fouling sensor of an apparatus for monitoring a fouling resistance and a cleanliness factor according to the present invention. As shown therein, a heating wire (about 14Ω) for generating heat is uniformly wound on an outer circumferential surface of the fouling sensor at a predetermined interval. The neighboring heating wires 11 are insulated by a ceramic insulation material 12 on an outer circumferential surface of the fouling sensor 10, and heat-transfer surface temperature measuring metal wires 13, each having a diameter of about 50~90 nm and formed of a Pt-wire having a purity of about 99.99%, are spirally wound on the whole outer circumferential surface of the fouling sensor 10 as much as the length corresponding to the resistance value (10~2,000Ω). The neighboring metal wires 13 are insulated by the ceramic insulation material 12. A sheath 14 formed of a stainless steel which serves as a heat-transfer surface is covered on the outer circumferential surface thereof.

At this time, the metal wire 13 is preferably made of Pt, Tungsten, Nickel, copper, or their alloy which has a high resistance temperature coefficient. More preferably, the metal wire 13 is made of a Pt wire which has an excellent characteristic that a resistance is linearly increased with respect to the increase of temperature. The lead wire of the metal wire 13 is connected with the accurate resistance measuring member 30, and the terminal of the interior heating wire 11 is connected with an external power supply member 20. At this time, when an alternating current is supplied to the heating wire 11, a current is inducted in the metal wire 13, and an error occurs in the measured electrical resistance value. A direct current electric power is preferably used for the power voltage supply member 20.

As a method for computing a heat load of the heating wire 11, there are two methods. A first method is to use a voltage and current which are supplied to the heating wire 11, and a second method is to use a temperature difference, water flow rate, and specific heat of water.

In the fouling monitoring apparatus according to the present invention, the voltage of the power supply member 20 is varied within a range of 10~240V, thus controlling the heat load which occurs in the interior of the fouling sensor 10, so that a heat load of the heat-transfer surface which corresponds to the operational condition of the heat exchanger is obtained and maintained. In addition, the weight of the deposits is increased as the flow rate of water is slow. Therefore, the amount of water is controlled by using the flowing water control valve 52 of the water amount control member, thus obtaining a predetermined flow rate which is similar to the field flow rate.

In addition, in the data calculation apparatus, the fouling resistance and the cleanliness factor are calculated by using the analog output signals which are generated from the fouling sensor 10, the inlet and outlet water temperature measuring member, the water flow rate measuring member, the power supply member 20, the accurate resistance measuring member, etc., and the computed results are automatically stored in the memory device of the calculation apparatus together with the measuring time.

If the metal wire 13 of the fouling sensor 10 is made of Pt, the temperature correcting method of the fouling sensor Pt wire will now be explained.

i) The resistance value of the fouling sensor Pt wire is measured at more than three points. At this time, an oil bath, which is generally used for correcting the temperature sensor, is used. The temperature of the oil bath is set to a predetermined level. The fouling sensor 10 is inserted into the oil bath, and a resistance value of Pt is accurately measured by using an accurate resistance measuring member 30 after a predetermined time lapse. The resistance value of Pt wire is measured at more than three points in the above-described manner, and then the measured temperature and resistance value are recorded.

ii) The temperature computation parameter value [IPTS-68 (international practical temperature scale 1968) coefficient] of Pt wire of the fouling sensor 10 is computed. A parameter is computed to measure the temperature based on the resistance value of Pt wire by using the temperature values and the resistance values which are computed by the above-described method. The temperatures and the resistance values which are obtained by the above-described method is inserted into the following equations, thus computing the parameter (IPTS-68 coefficient).

$$R_t = R_o \times [1 + \alpha \times \{T - \delta \times (T/100) \times (T/100 - 1)\}]$$

where T denotes a temperature (°C),
R$_t$ denotes a resistance (Ω) of a Pt wire, and
R$_0$, α, δ denote parameter constant values.

The temperature computation parameter values of the Pt wire of the fouling sensor 10 which is used for the fouling monitoring apparatus, are as follows.

R$_o$ = 190.105 Ω
α = 3.92572×10$^{-3}$
δ = 7.30819 iii) The method of using the temperature measure parameter values computed by the above-described method is as follows. The temperature measure parameter computed by the method (ii) is inputted into the accurate resistance measuring member 20, thus displaying a temperature as digits which corresponds to the resistance value of the fouling sensor Pt wire, and the output signal (voltage) is transferred to the data calculation apparatus according to the present invention for computing the fouling resistance and the cleanliness factor. The temperature values which are measured in the above-described manner denotes an average temperature value of the heat-transfer surface.

The computation which is performed in the data calculation apparatus of the fouling monitoring apparatus according to the present invention will now be explained.

The analog transmission signals of 0~10V and 4~20 mA transferred from various measuring sensors and units are transmitted to the calculation apparatus. The fouling resistance and a cleanliness factor are computed. At this time, the measured data are automatically stored into the memory device of the data calculation apparatus 61 at a predetermined time interval, and the current measuring data and the computation results are displayed on the monitor or printed by the printer 62, so that a computed program is fabricated in order to monitor the fouling resistance in real time. In addition, it is possible to remotely observe the measured data and computation results by using the modem 71.

i) The calculation of the heat load (Units: W, Btu/hr, kcal/sec)

Method 1: Q=water specific heat×the amount of flowing water×(outlet temperature−inlet temperature)

Method 2:

$Q$ = voltage× current

= (voltage)$^2$ / resistance of heating wire ii) The calculation of an overall heat transfer coefficient (Units: W/cm$^2$/°C., Btu/ft$^2$/hr/F, kcal/cm$^2$/hr/°C.) on the start time:

$$U_1 = 1/(1/h + x/k) = Q_1/(A \times \Delta T_{m1})$$

on the predetermined time:

$$U_2 = 1/(1/h + x/k + R_f) = Q_2/(A \times \Delta T_{m2})$$

where A denotes a heating element area,
x denotes the thickness of a heat-transfer surface of a metal;
h denotes a film heat transfer coefficient,
k denotes a heat-transfer coefficient of a metal of a heat-transfer surface,
Q$_1$ denotes the heat flow rate at an initial stage of measuring,
Q$_2$ denotes the heat flow rate after a time lapse of t,
U$_1$ denotes an overall heat transfer coefficient on initial stage of measuring,
U$_2$ denotes an overall heat transfer coefficient after a time lapse of t,
ΔT$_{m1}$ denotes an average temperature difference between a water and a heat-transfer surface at an initial stage, and
ΔT$_{m2}$ denotes an average temperature difference between a water and a heat-transfer surface after a time lapse of t.

iii) The computation of the fouling resistance coefficient (R$_f$) (Units: °C..cm$^2$/W, F.ft$^2$.hr/Btu, °C..cm$^2$ hr/kcal)

$$R_f = 1/U_2 - 1/U_1$$

iV) The computation of a cleanliness factor (CF) (unit: %)

$$CF = U_2/U_1 \times 100$$

EXAMPLE

The fouling resistance and the cleanliness factor on the heat-transfer surface of the heat exchanger were measured under the following conditions while the condition of the water flow rate was being varied by using an apparatus for monitoring a fouling resistance according to the present invention.

Experiment condition:

| Water quality: | Ca$^{+2}$ | 236 ppm as CaCO$_3$ |
|---|---|---|
| | So$_4^{-2}$ | 220 ppm as CaCO$_3$ |
| | Mg$^{+2}$ | 86 ppm as CaCO$_3$ |
| | Cl$^-$ | 210 ppm as CaCO$_3$ |
| | Na$^+$ | 350 ppm as CaCO$_3$ |
| | SiO$_2$ | 3 ppm as SiO$_2$ |
| | HCO$_3^-$ | 223 ppm as CaCO$_3$ |

Heat load of heat-transfer surface: 15W/cm$^2$
Water flow rate on heat-transfer surface: 3 ft/sec, 5 ft/sec, 7 ft/sec
Metal material of heat-transfer surface: SUS 304

The monitored results of a fouling resistance and a cleanliness factor when the scale deposition reaches at equilibrium as shown in Table 3.

TABLE 3

The results of a fouling resistance and a cleanliness factor

| Classification\ Number of Testings | Flowing speed of water (ft/sec) | Time for reaching balance | Cleanness level coefficients measured (× 10$^{-4}$, ° C. · m$^2$/W) | Cleanness level measured (%) | Pollution level evaluation result |
|---|---|---|---|---|---|
| 1 | 3 | 500 | 5.3 | 80 | Improper |
| 2 | 5 | 600 | 4.6 | 82 | Should be |

TABLE 3-continued

The results of a fouling resistance and a cleanliness factor

| Classification\ Number of Testings | Flowing speed of water (ft/sec) | Time for reaching balance | Cleanness level coefficients measured ($\times 10^{-4}$, $°$ C. $\cdot$ m$^2$/W) | Cleanness level measured (%) | Pollution level evaluation result |
|---|---|---|---|---|---|
| 3 | 7 | 1,500 | 3.3 | 87 | improved Good |

*Based on $5.1 \times 10^{-4}$ $°$ C. $\cdot$ m$^2$/W as the allowable value of the fouling resistance of the heat-transfer surface As shown in Table 3, as a result of the measuring of the fouling resistance coefficient, as the water flow rate was increased, the fouling resistance was decreased. In addition, the time of reaching a predetermined amount of the scales formed was increased. In addition, when the flow rate was 7 ft/sec, the fouling resistance coefficient was within the effective reference value, and when the flow rate was 3 ft/sec, it was judged that another water treatment method is needed such as a method of improving water quality or using a scale inhibitor. In addition, as a result of the test performance of the apparatus for monitoring fouling resistance, the accuracy of the measured data and the reproductivity were excellent, so that the data were available for the use in the industry. It was possible to improve the efficiency of the heat exchanger and reduce the maintenance and operational costs.

As described above, the apparatus for monitoring fouling resistance on a heat-transfer surface of a heat exchanger and a method thereof according to the present invention is well applicable to optimizing a water quality control, determining a proper cleaning period of a heat exchanger, and computing an operation efficiency of the apparatus by continuously monitoring a fouling resistance such as a deposit formation in the heat exchanger by adapting the apparatus according to the present invention to a petrochemical factory or a power plant.

In addition, in the apparatus for monitoring fouling resistance on a heat-transfer surface of a heat exchanger and a method thereof according to the present invention, it is possible to detect a small amount of deposit formation on a heat-transfer surface of a heat exchanger due to impurities contained in a cooling system of the heat exchanger. Furthermore, it is possible to continuously and accurately check a fouling resistance and a cleanliness factor of the heat exchanger without an error.

Although preferred embodiments of the present invention have been disclosed for illustrative purposes, those skilled in the art will appreciate that various modifications, additions and substitutions are possible without departing from the scope and spirit of the invention as recited in the accompanying claims.

What is claimed is:

1. An apparatus for monitoring a fouling resistance or a cleanliness factor of a heat-transfer surface, comprising:
    a fouling sensor for measuring an average temperature of heat-transfer surface as a resistance value of metal wire which is uniformly wound inside the heat-transfer surface;
    an electrical resistance measuring means for measuring an electrical resistance of the metal wire;
    a temperature measuring means for measuring water temperatures of inlet/outlet portions of the apparatus;
    a flow rate measuring means for measuring the water flow rate flowing into the apparatus;
    a data calculation means for computing a fouling resistance or a cleanliness factor of the heat-transfer surface with using analog output signals from the electrical resistance measuring means of the fouling sensor, the inlet/outlet water temperature measuring means and the water flow rate measuring means.

2. The apparatus of claim 1, wherein a heating wire is uniformly wound on an inner surface of the fouling sensor, neighboring heating wires are insulated by electrical insulation materials, an outer surface of the heating wire is wound by a given length of metal wire corresponding to a predetermined resistance value, neighboring metal wires are insulated by electrical insulation materials, and an outer surface of the metal wire is covered with a heat-transfer material or a heat-transfer metal.

3. The apparatus of claim 2, including a direct current power source supplying device for supplying direct current to said heating wire, the heat load on the heat-transfer surface of the fouling sensor being controlled by varying the voltage of the direct current power source supplying device.

4. The apparatus of claim 1, wherein said inlet and outlet water temperature measuring means are respectively provided with an inlet temperature sensor and signal transmitter, and an outlet temperature sensor and signal transmitter.

5. The apparatus of claim 1, wherein said water flow rate measuring means are provided with a flow sensor, a flow controller and a flow control valve.

6. The apparatus of claim 1, wherein said data calculation apparatus includes:
    a data calculation apparatus having a memory device; and
    a monitor for displaying a currently measured data and a calculation result or a printer for printing the result of the computation.

7. The apparatus of claim 1, including a modem to which said data calculation apparatus is connected so that measured data and calculation results which are obtained by the fouling monitoring apparatus can be observed by a remote personal computer.

8. The apparatus of claim 1, wherein said metal wire is selected from the group consisting of platinum, tungsten, nickel, copper and alloys thereof.

9. A method for measuring a fouling resistance or a cleanliness factor of a heat-transfer surface, comprising the steps of:
    disposing a metal wire having a high resistance temperature coefficient around a heat-transfer surface;
    measuring an electrical resistance variation of the metal wire;
    measuring an average temperature of a heat-transfer surface based on the electrical resistance value of the metal wire; and
    computing a fouling resistance or a cleanliness factor of the heat-transfer surface.

10. An apparatus for monitoring scale build up on a heat transfer surface exposed to water flowing thereover which comprises:

a housing defining an inlet and an outlet to enable water to flow therethrough, an inlet temperature-measuring means for measuring the temperature of water flowing into said housing, an outlet temperature-measuring means for measuring the temperature of water flowing out of said housing, a flow rate-measuring means for measuring the flow rate of water flowing through said housing, a fouling sensor located in said housing between said inlet and said outlet, said fouling sensor defining a heat-transfer surface and containing within said heat-transfer surface a coiled heating wire and a coiled metal wire, said coiled metal wire being located between said coiled heating wire and said heat-transfer surface, an electrical power supply means connected to said heating wire, a resistance-measuring means connected to said metal wire, and a data calculation means to which said inlet temperature-measuring means, said outlet temperature-measuring means, said flow rate-measuring means, said electrical power supply means and said resistance-measuring means are connected, said data calculation means computing scale built up on said heat transfer surface.

* * * * *